US00PP20242P2

(12) United States Plant Patent
Danziger

(10) Patent No.: US PP20,242 P2
(45) Date of Patent: Sep. 1, 2009

(54) ***TORENIA* PLANT NAMED 'DANCAT266'**

(50) Latin Name: *Torenia*
Varietal Denomination: DANCAT266

(75) Inventor: Gabriel Danziger, Moshav Nir-Zvi (IL)

(73) Assignee: Danziger 'Dan' Flower Farm, Post Beit Dagan (IL)

( * ) Notice: Subject to any disclaimer, the term of this patent is extended or adjusted under 35 U.S.C. 154(b) by 0 days.

(21) Appl. No.: 12/150,975

(22) Filed: May 2, 2008

(51) Int. Cl.
*A01H 5/00* (2006.01)

(52) U.S. Cl. ..... Plt./487
(58) Field of Classification Search ..... Plt./487

See application file for complete search history.

(56) References Cited

PUBLICATIONS

Publication by the Canadian PBRO Plant Varieties Journal Extranet (Apr. 2008, No. 67) which lists the application particulars for the corresponding, international PBRO application No.: CA 08–6231 filed Mar. 27, 2008 (1 pg.) (http:/www.inspection.gc.ca/english/plaveg/pbrpov/cropreport/tor/app00007228e.shtml).

*Primary Examiner*—Annette H Para
(74) *Attorney, Agent, or Firm*—Foley & Lardner LLP

(57) ABSTRACT

A new and distinct *Torenia* plant named 'DANCAT266' particularly characterized by plenty of delicate, funnel form, cup-shaped flowers with petals in shades of light yellow with yellow blotch on lower petal; cascading bush, which maintains a compact, rounded plant habit; vigorous growth habit; densely branched plant, gracefully cascading from hanging baskets; early flowering response and stays in full bloom in moderate climate; suitable as an annual for hanging pots outdoors under partial shade and good weather tolerance with a preferred temperature range of 15° C. to 25° C.

2 Drawing Sheets

Latin name of the genus and species of the plant claimed: *Torenia* sp.
Variety denomination: 'DANCAT266'.

BACKGROUND OF THE INVENTION

The present invention relates to a new and distinct cultivar of *Torenia* plant, botanically known as *Torenia* sp. of the *Scrophulariaceae* family, and hereinafter referred to by the cultivar name 'DANCAT266'

The new *Torenia* cultivar is a product of a planned breeding program conducted by the inventor, Gabriel Danziger, in Moshav Mishmar Hashiva, Israel. The objective of the breeding program was to develop a new *Torenia* cultivar with unique yellow flowers.

The new *Torenia* cultivar originated from an induced mutation by gamma rays of the *Torenia* designated 'TR-5-134' (unpatented). made in a controlled breeding program by the inventor, Gabriel Danziger, in 2006 in Moshav Mishmar Hashiva, Israel. The new *Torenia* cultivar was discovered and selected by the inventor, Gabriel Danziger, as a single flowering plant within the progeny of the stated mutation in a controlled environment in May of 2006 in Moshav Mishmar Hashiva, Israel.

Asexual reproduction of the new *Torenia* cultivar by soft cuttings was first performed in June of 2006 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'DANCAT266' which in combination distinguish this *Torenia* as a new and distinct cultivar:

1. Plenty of delicate, funnel form, cup-shaped flowers with petals in shades of light yellow with yellow blotch on lower petal;
2. Cascading bush, which maintains a compact, rounded plant habit;
3. Vigorous growth habit;
4. Densely branched plant, gracefully cascading from hanging baskets;
5. Early flowering response and stays in full bloom in moderate climate;
6. Suitable as an annual for hanging pots outdoors under partial shade; and
7. Good weather tolerance with a preferred temperature range of 15° C. to 25° C.

Plants of the new *Torenia* 'DANCAT266' differ from plants of the parental cultivar, *Torenia* 'TR-5-134' (unpatented) in the characteristics described in Table 1.

TABLE 1

| Characteristic | New Cultivar 'DANCAT266' | Parental Cultivar TR-5-134 (unpatented) |
|---|---|---|
| Mature Flower color | Petal shades of light yellow, with a yellow blotch on lower petal | Petal shades of dark violet, with a yellow blotch on lower petal |
| Flower size | Depth: About 2 cm<br>Width: About 3.5 cm | Depth: About 3 cm<br>Width: About 3 cm |
| Growth habit | Cascading bush | Trailing |
| Flowering Response Time | 7 weeks from planting | 9 weeks from planting |

Of the many commercial cultivars known to the present inventor, the most similar in comparison to the new *Torenia* 'DANCAT266' is the *Torenia* 'DANMOON16' (patented, U.S. Plant Pat. No. 18,333), in the characteristics described in Table 2.

TABLE 2

| Trait | New Cultivar 'DANCAT266' | Comparison Cultivar 'DANMOON16' (patented, U.S. PP18,333) |
|---|---|---|
| Mature Flower Color | Petal shades of light yellow (RHS 5A, RHS 5C and RHS 6A), with a yellow blotch (RHS 7A) on lower petal and a purple throat (RHS 77A)t | Petal shades of yellow (RHS 7A), with no yellow blotch on lower petal and a purple throat (RHS N79A and RHS 70B) |
| Flower size | Depth: About 2 cm Width: About 3.5 cm | Depth: About 3.0 cm Width: About 3.2 cm |
| Growth habit | Cascading bush | Cascading bush |
| Flowering Response Time | 7 weeks from planting | 3 weeks from planting |

BRIEF DESCRIPTION OF THE PHOTOGRAPHS

The accompanying photographs illustrate the overall appearance of the new *Torenia* 'DANCAT266' showing the colors as true as is reasonably possible with colored reproductions of this type. Colors in the photographs may differ slightly from the color values cited in the detailed botanical description, which accurately describe the color of 'DANCAT266'.

DETAILED BOTANICAL DESCRIPTION

Figure 1:
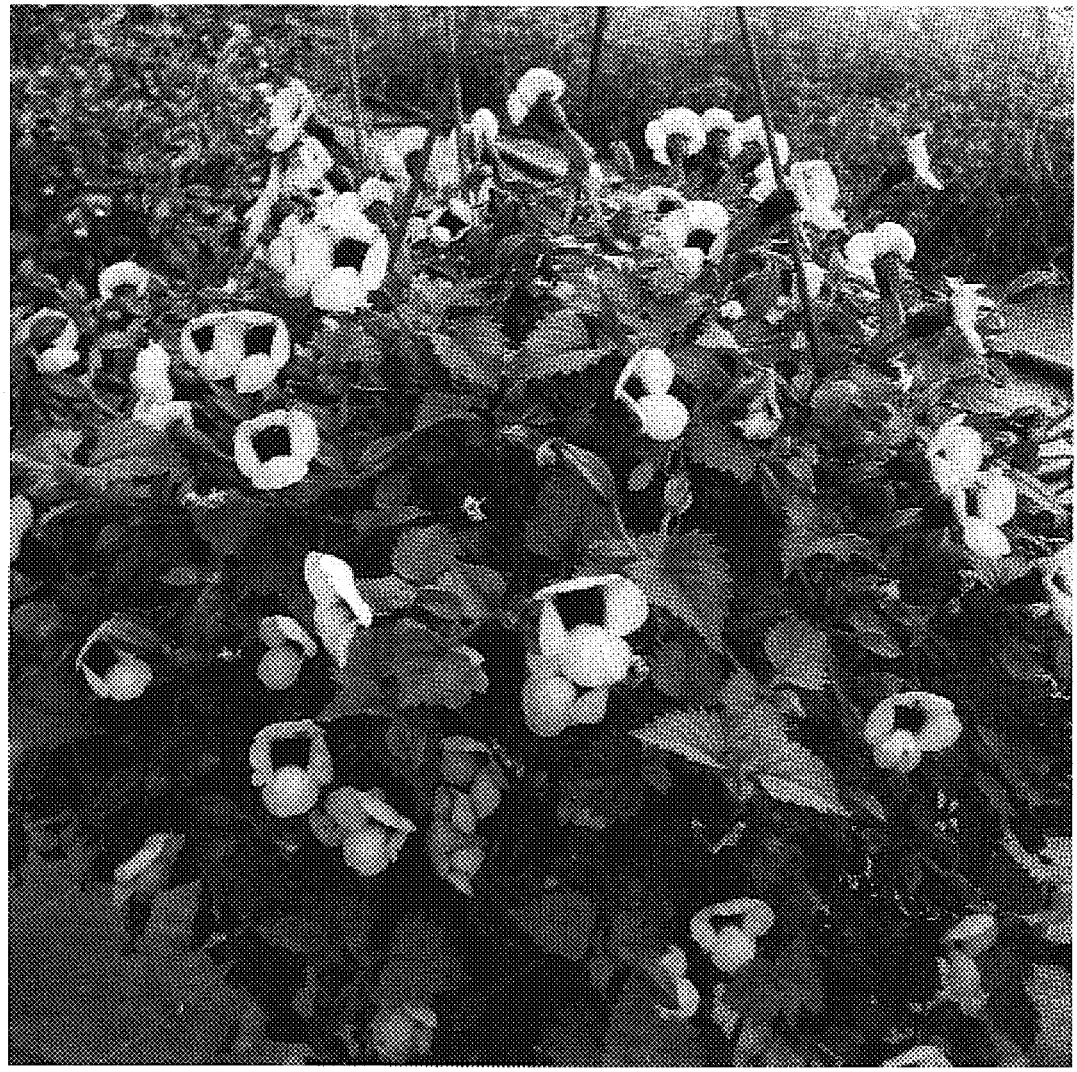
FIG. 1 shows a side perspective view of a typical flowering plant of 'DANCAT266' in a hanging planter at 2 months of age.
Figure 2:
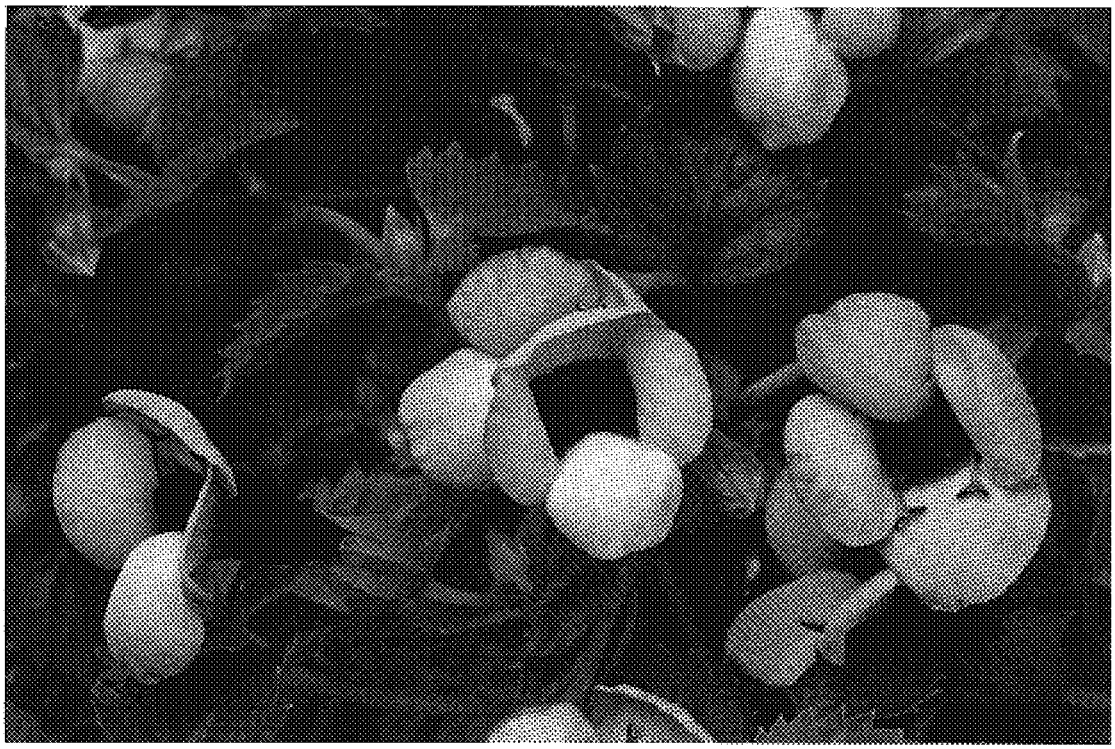
FIG. 2 shows a close-up of the typical flowers, buds and leaves of 'DANCAT266' at 2 months of age.

The new *Torenia* 'DANCAT266' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'DANCAT266' as grown in a greenhouse in Moshav Mishmar Hashiva, Israel, under conditions which closely approximate those generally used in commercial practice. Optimal growth conditions include that plants of 'DANCAT266' are grown outdoors in a moderate climate and indoors during the winter season. Irrigation and fertilization are recommended on a regular basis. Plants of 'DANCAT266' are usually grown in full sunlight, but partial shade is required in mid summer. Plants of 'DANCAT266' are fully grown in 2 months from planting a cutting in the summer season and bloom all year-round in a moderate climate. The 'DANCAT266' plants described herein were grown indoors in 13 cm pots in a glass greenhouse in Moshav Mishmar Hashiva, Israel, with the day temperatures ranging from 18° C. to 35° C. and night temperatures ranging from 16° C. to 25° C. Plants of 'DANCAT266' were fertilized with level of 150 ppm N.

Color references are made to The Royal Horticultural Society Colour Chart (R.H.S.), 2001 edition, except where general colors of ordinary significance are used. Color values were taken under daylight conditions at approximately noon in Moshav Mishmar Hashiva, Israel. The age of the 'DANCAT266' plants described is 7 weeks.

Parentage: *Torenia* designated 'TR-5-134' (unpatented).
Propagation: Tissue culture and soft tip cuttings.
Plant:
- *Form.*—Bush, cascading.
- *Growth habit.*—Rounded.
- *Height.*—About 10 cm to 20 cm.
- *Spread.*—About 20 cm to 35 cm.
- *Cold tolerance.*—Frost tender. Temperatures below 5° C. may damage plants.
- *Vigor.*—Vigorous growth; plants are fully grown in 2 months from planting cutting in during summer season.

Stem:
- *Color.*—Yellow-green, RHS 144A.
- *Length.*—About 20 cm.
- *Diameter.*—About 2 mm.
- *Pubescence.*—Minimal.
- *Branching.*—About 3 to 5 main branches grow from the base and split into hundreds of secondary and tertiary branches.
- *Length of internodes.*—About 2 cm to 6 cm.

Foliage:
- *Overall shape.*—Triangular.
- *Apex.*—Acute.
- *Base.*—Cordate.
- *Size of leaf.*—Width: About 1.5 cm to 2.5 cm. Length: About 1.5 cm to 3.5 cm.
- *Margin.*—Serrate.
- *Color (mature).*—Center color of leaf: Green, RHS 137A. Upper side: Green, RHS 137A. Under side: Yellow-green, RHS 146A.
- *Color (immature).*—Center color of leaf: Green, RHS 137B. Upper side: Green, RHS 137B. Under side: Yellow-green, RHS 146A.
- *Leaf texture.*—Upper: Pubescence. Under: Pubescence.
- *Venation.*—Pattern: Anastomotic. Color: Upper surface: Green, RHS 137A. Lower surface: Green, RHS 137C.
- *Petioles.*—Length: About 0.5 cm to 1.0 cm. Diameter: About 2.0 mm. Color: Green, RHS 143A.

Flowers:
- *Blooming period.*—All year round in a moderate climate or in a greenhouse environment. In Israel, flowering occurs between March and November outdoors.
- *Flowering response time.*—About 7 weeks from planting.
- *Flowering stem.*—Flowers appear along the growing stems.
- *Quantity of flowers.*—Per stem: About 5 to 10; Per plant: About 40 to 60.
- *Flowering longevity.*—On the plant: About 4–7 days. Depend on temperature. Vase life: not relevant.
- *Type.*—Single.
- *Shape.*—Overall: funnel form; 5-winged;, Corolla tube: cylindrical or often broadened above; Corolla: 2-lipped, the upper lip faintly 2-lobed, the lower lip 3-lobed.
- *Orientation at opening.*—Slanted upward.
- *Fragrance.*—None.
- *Flower size.*—Depth: About 2.0 cm. Width: About 3.5 cm.

*Bud.*—

*Shape.*—Oblong, cylindrical, ellipsoid, 5-winged.

*Size.*—Length: About 1.5 cm. Diameter: About 1.0 cm.

*Color.*—Apex: Green, RHS 137B. Base: Green, RHS 137B. Middle: Green, RHS 137B.

*Texture.*—Pubescence on winged edges.

*Floral tube.*—Length: About 2.5 cm. Width: About 0.5 cm to 1.0 cm. Color: Outside: Violet, RHS 83B (apex), violet, RHS 83A (middle) and green-yellow, RHS 1C (base). Inside: Green-yellow, RHS 1D (apex), purple-violet, RHS N81A (middle), and purple-violet, RHS N81A (base).

*Petals.*—Number: Four, fused. Length: Upper Petal: About 1.5 cm; Side Petals: About 1.0 cm; Lower Petal: About 1.0 cm. Width: Upper Petal: About 2.0 cm; Side Petals: About 1.0 cm; Lower Petal: About 1.5 cm. Shape: Upper Petal: Overall: spatulate, Apex: rounded, Base: fused; Side Petals: Overall: spatulate, Apex: rounded, Base: fused; Lower Petal: Overall: spatulate, Apex: rounded, Base: fused. Margin: Undulated. Color: All petals with yellow color, and a dark yellow blotch in the middle of the lower petal near base. Mature Petals: Upper Surface: Upper Petal: Yellow: near apex, RHS 5A, and near base, RHS 5C; and margin, RHS 5A; Side Petals: Yellow: near apex, RHS 6A, with centralized RHS 6A, and near base, RHS 6A, and margin RHS 5A; Lower Petal: Yellow: primarily RHS 6A, with RHS 7A blotch in the middle near base, and RHS 6A color surrounding blotch and near base, and margin RHS 6A. Lower Surface: Upper Petal: Yellow: near apex, RHS 5A, and near base, RHS 5A and margin, RHS 5A; Side Petals: Yellow: near apex, RHS 5A, and near base, RHS 5C and margin, RHS 5A; Lower Petal: Yellow: near apex, RHS 5B, and near base, RHS 5B and margin, RHS 5B. Throat: Upper throat: Purple, RHS 77A; Lower throat: Purple, RHS 77A. Immature Petals: Upper Surface: Upper Petal: Yellow: near apex, RHS 6A, and near base, RHS 6A; and margin, RHS 6A; Side Petals: Yellow: near apex, RHS 6A, near base, RHS 6A, and margin RHS 6A; Lower Petal: Yellow: primarily RHS 6A, with RHS 6A blotch in the middle near base, and margin RHS 6A. Lower Surface: Upper Petal: Yellow: near apex, RHS 6A, and near base, RHS 6A and margin, RHS 6A; Side Petals: Yellow: near apex, RHS 6A, and near base, RHS 6C, and margin, RHS 6A; Lower Petal: Yellow: near apex, RHS 6C, and near base, RHS 6C and margin, RHS 6C; Throat: Center of Flower: Purple, RHS N79D.

*Sepals.*—Number: 5. Length: About 1.5 cm. Width: About 0.5 cm to 1.0 cm. Shape: Two-lobed, 5-winged. Apex: Acute. Base: Wedge shaped. Margin: Entire. Color: Green, RHS 137C.

*Peduncle.*—Length: About 0.5 cm to 1.5 cm. Diameter: About 2.0 mm. Color: Yellow-green, RHS 144A.

Reproductive organs:

*Androecium.*—Stamen: Number: 2 pairs per flower, fused. Color: Purple, RHS N79C. Anther: Length: About 0.3 cm; Width: About 0.1 cm. Color: Purple, RHS 79A. Spur: Not Present. Filament: Length: About 1.0 cm; upper anther shorter— about 0.5 cm Width: About 0.1 cm. Color: Violet, RHS 84C. Pollen: Amount: Moderate Color: White, RHS N155D. Requirements for pollination: Young flowers, active pollen, and receptive, open stigma.

*Gynoecium.*—Pistil: Number: One per flower. Length: About 2.4 cm. Stigma: Length: About 0.3 cm. Width: About 0.2 cm. Color: Violet, RHS 84C. Style: Length: About 1.9 cm. Color: Purple, RHS 75C. Ovary: Number: 1. Length: About 0.5 cm. Width: About 0.2 cm. Color: Green, RHS 143B.

Seed/fruit: None.

Pest/disease resistance and/or susceptibility: A standard preventative spray program is sufficient as no susceptibility was observed.

Temperature tolerance: Sensitive to temperatures below 5° C.

I claim:

1. A new and distinct *Torenia* plant named 'DANCAT266', as illustrated and described herein.

* * * * *